United States Patent
Chen

(10) Patent No.: US 6,865,948 B1
(45) Date of Patent: Mar. 15, 2005

(54) METHOD OF WAFER EDGE DAMAGE INSPECTION

(75) Inventor: Sheng-Hsiung Chen, Taichung (TW)

(73) Assignee: Taiwan Semiconductor Manufacturing Company, Hsin-Chu (TW)

( * ) Notice: Subject to any disclaimer, the term of this patent is extended or adjusted under 35 U.S.C. 154(b) by 0 days.

(21) Appl. No.: 10/059,835

(22) Filed: Jan. 29, 2002

(51) Int. Cl.⁷ .......................... G01N 29/08; G01N 21/88
(52) U.S. Cl. .............................. 73/597; 73/599; 73/602; 250/559.42; 356/237.5
(58) Field of Search .......................... 73/597, 598, 599, 73/600, 601, 602, 620; 250/559.01, 559.42; 356/237.1–237.6

(56) References Cited

U.S. PATENT DOCUMENTS

| | | | | |
|---|---|---|---|---|
| 4,011,748 A | * | 3/1977 | Bond et al. .................... | 73/601 |
| 4,366,713 A | * | 1/1983 | Gilmore et al. ............... | 73/618 |
| 4,741,212 A | * | 5/1988 | Rehwald ....................... | 73/600 |
| 4,803,884 A | * | 2/1989 | Kaneta et al. ................ | 73/598 |
| 5,479,252 A | * | 12/1995 | Worster et al. ........... | 356/237.5 |
| 5,592,295 A | * | 1/1997 | Stanton et al. ............... | 356/426 |
| 5,797,845 A | | 8/1998 | Barabash et al. ........... | 600/443 |
| 5,955,673 A | | 9/1999 | Leroy et al. .................. | 73/602 |
| 6,045,434 A | | 4/2000 | Fisher, Jr. et al. .............. | 451/6 |
| 6,062,084 A | * | 5/2000 | Chang et al. ................. | 73/601 |
| 6,188,050 B1 | | 2/2001 | Duffer et al. ............... | 219/497 |
| 6,356,346 B1 | * | 3/2002 | Hagen et al. ............. | 356/237.1 |
| 6,545,752 B1 | * | 4/2003 | Swan et al. .............. | 356/237.4 |

* cited by examiner

Primary Examiner—Hezron Williams
Assistant Examiner—Rose M. Miller
(74) Attorney, Agent, or Firm—Thomas, Kayden, Horstemeyer & Risley

(57) ABSTRACT

A source of ultrasound waves or energy is directed at the wafer that is to be inspected in a direction that is essentially perpendicular with the surface of the wafer. The ultrasonic waves are intercepted and analyzed after these waves have passed through the wafer that is being inspected. From this analysis and comparing the captured waves or ultrasonic energy with the emitted ultrasonic waves, conclusions can be drawn on defects and other irregularities that are present in the medium, that is the wafer, through which the ultrasonic waves have passed.

22 Claims, 4 Drawing Sheets

METHOD OF WAFER EDGE DAMAGE INSPECTION

BACKGROUND OF THE INVENTION (1) Field of the Invention

The invention relates to the fabrication of integrated circuit devices, and more particularly, to a method for the inspection of damage that is incurred in the perimeter or edge of a wafer during and as a result of wafer processing.

(2) Description of the Prior Art

The creation of semiconductor devices uses large-diameter silicon wafers that have been created by separating or cutting these wafer from silicon ingots of cylindrical shape. For the handling of the created wafers, methods of automation are applied whereby the wafers are mounted in for instance wafer cassettes or wafer boats. Wafer cassettes and wafer boats are typically used for the transportation of wafers from one processing station to another processing station, for the storage of wafers, for storage of wafers as part of a temporary interruption of a processing sequence, for loading and positioning wafers in a processing chamber. On other occasions, wafers are positioned into a processing location by robotic controlled lifting and positioning devices or are moved through a processing station using automatic methods (such as a conveyer belt) of positioning the wafer into, within and exiting from a processing station.

Most of these operations require a physical interface between the wafer that is being transported and the transporting interface. To facilitate this physical interface, a surface area around the perimeter of the wafer is typically not used for the creation of semiconductor devices but is reserved exclusively as a means of handling the wafer.

Many of the tools and mechanisms that are used for the transportation of wafers are of a sophisticated nature and are carefully crafted with the objective of minimizing or avoiding any damage that can potentially occur in the surface (perimeter) of the wafer where the physical contact with the wafer is typically established. Despite these delicate and sophisticated methods that are used for transporting wafers, wafer damage of some sort is to be expected, which imposes the need for wafer inspection at critical points in the chain of wafer transportation.

Wafer inspection, which has as objective to detect and identify damage that is incurred by the wafer in the transportation and handling thereof, is typically performed by visually inspecting the wafer for damage. This method is however open to human error or oversight and can therefore be improved, thus eliminating unnecessary wafer loss or oversight of existing wafer damage.

The invention provides such a method of inspecting wafers by eliminating visual, operator performed inspection of wafers. By applying an ultrasound-based methodology, the inspecting of wafers can be significantly improved with regard to accuracy and speed and throughput of inspection.

U.S. Pat. No. 5,955,673 (Leroy et al.) shows an ultra sound inspection method for a cathode target.

U.S. Pat. No. 6,188,050 (Duffer et al.) describes a laser ultrasonic application as a way to measure wafer temperature.

U.S. Pat. No. 6,045,434 (Fisher, Jr. et al.) shows an ultrasound method to monitor CMP pad life.

U.S. Pat. No. 5,797,845 (Barabash et al.) shows an ultrasound imaging technique.

SUMMARY OF THE INVENTION

A principle objective of the invention is to improve the method of wafer inspection.

Another objective of the invention is to reduce the occurrence of wafer breakage that is due to defective wafers having passed wafer inspection.

Yet another objective of the invention is to improve the accuracy of wafer inspection.

A still further objective of the invention is to improve the throughput of wafer inspection.

A still further objective of the invention is to enable automation of wafer inspection.

In accordance with the objectives of the invention a new method is provided for the inspection of wafers for physical damage. Previous methods of wafer inspection have been based on visual inspection of the wafer, the invention provides for inspection of wafers using ultrasound technology. A source of ultrasound waves or energy is directed at the wafer that is to be inspected in a direction that is essentially perpendicular with the surface of the wafer. The ultrasonic waves are intercepted and analyzed after these waves have passed through the wafer that is being inspected. From this analysis and comparing the captured waves or ultrasonic energy with the emitted ultrasonic waves, conclusions can be drawn on defects and other irregularities that are present in the medium, that is the wafer, through which the ultrasonic waves have passed.

DESCRIPTION OF THE PREFERRED EMBODIMENTS

Figure 1:
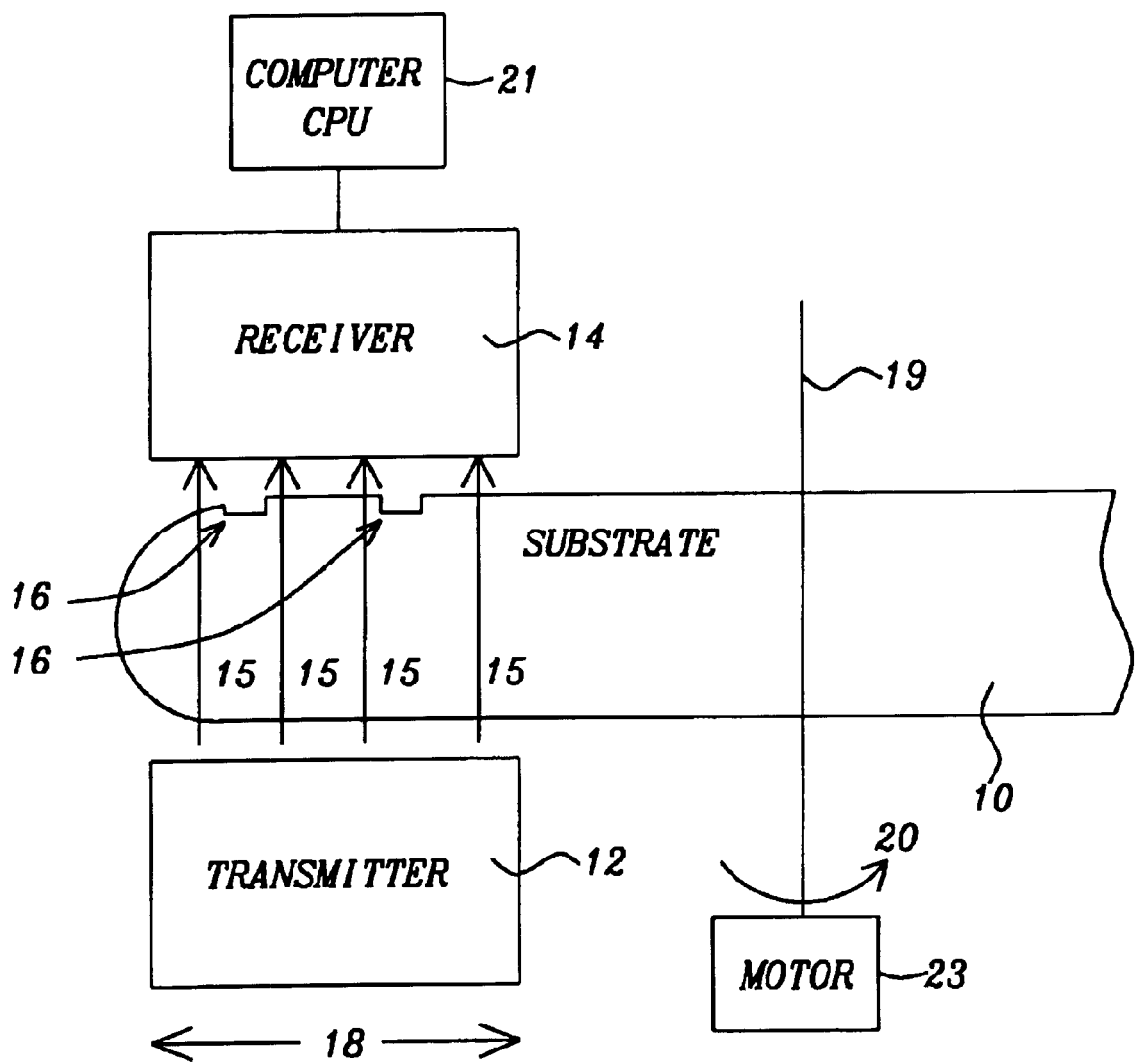
FIG. 1 is a cross section of a wafer with ultrasonic equipment arranged around the surface thereof. A computer Central Processing Unit (CPU) is part of the equipment arrangement.

The use of ultrasonic equipment and the application of this equipment for various industrial applications can be highlighted as follows:

Waves, comprising such wave identifying wave characteristics as amplitude, frequency and phase, are send or transmitted by a transmitter The transmitted waves are allowed to impact and pass through a medium that is being investigated for certain characteristics such as density of material, the presence of a material, the temperature of a known material as reflected in the density of the material, the composition of a material, and the like The transmitted waves, after these waves have passed through the medium that is being investigated, are captured and analyzed, and From the latter analysis, conclusions are drawn that relate to the sought after or investigated characteristic of the medium that is being investigated.

If ultrasonic waves pass through a medium that is being investigated in a uniform manner, it may properly be concluded that the density of the medium that is being investigated is uniform. That is, no such non-uniform medium characteristics as cracks, fissures or a sudden or gradual change in density of the investigated medium is part of the investigated medium.

If on the other hand ultrasonic waves pass through a medium that is being investigated in a non-uniform manner, it may properly be concluded that the density of the medium that is being investigated is not uniform. That is, non-uniform medium characteristics such as cracks, fissures or a sudden or gradual change in density of the investigated medium are part of the investigated medium.

Typical wafer damage can be characterized as being surface irregularities such as surface scratching, complete or partial breaking of the wafer and the like. For this type of wafer damage therefore, the density of the wafer is changed with respect to the density of surrounding wafer material, causing an irregular passing through the wafer of energy of an ultrasonic nature. By therefore analyzing ultrasonic waves after these waves have passed through a medium such as a wafer, this passing having been implemented in a manner of perpendicularly impacting the surface of the wafer with ultrasonic waves and in passing the ultrasonic waves through the wafer from a first surface to a second surface of which the edge of the wafer may be a part, conclusions can be drawn that relate to the uniformity of the passed-through medium, that is the wafer.

This analysis may or may not comprise thereby including characteristics of the transmitted waves prior to the event of having these waves impacting the medium under investigation. By including these original waves in the analysis a quantitative measure may be gained relating to the degree of irregularity or irregularities that is present in the medium that is being investigated.

By excluding these original waves, the presence of irregularity or irregularities can be detected in the medium that is being investigated by for instance detecting a shift in frequency distribution, an irregular modification of the amplitude of the received or captured ultrasonic waves, a phase-shift in the received or captured waves, and the like.

With the above highlighted characteristics in mind, the cross-section that is shown in FIG. 1 will now be discussed.

Highlighted in the cross section of FIG. 1 are the following elements:

10, a cross section of a semiconductor substrate that is being investigated for irregularities over or within the surface thereof 12, a first component of a receiving-transmitting arrangement, in this instance based on ultrasonic technology, whereby component 12 represents a transmitter of the ultrasonic arrangement 14, a second component of the receiving-transmitting arrangement, in this instance based on ultrasonic technology, whereby component 14 represents a receiver of the ultrasonic arrangement; it is assumed that receiver 14 comprises capabilities of analysis of the waves that are received by this unit 15, waves, in this instance of an ultrasonic waves, that are emitted or transmitted by transmitter 12, thereupon pass through the wafer 10 in a direction that is perpendicular with a surface of wafer 10 after which waves 15 are intercepted or received by receiver 14 for purposes of wave analysis 16, examples of surface irregularities that may appear in a surface of wafer 10

18, an estimated distance over the surface of wafer 10 over which surface irregularities can be expected to occur; a typical number for this distance is about 5 mm 19, the central axis of the wafer 10, emanating from the wafer 10 in a direction that is perpendicular with a surface of wafer 10 and further comprising the center of a circle that contains 20, a direction in which wafer 10 is advanced in a rotating motion having the central axis 19 as the center of rotation, 21, a computer controller or processor CPU, and 23, a rotary motor which imparts rotating motion 20 to semiconductor substrate 10.

From the cross section that is shown in FIG. 1, it is clear that if the wafer 10 were to remain in a stationary position whereby surface irregularities 16 are confined to the plane of the cross section that is shown in FIG. 1, only surface irregularities 16 would be in a position of analysis, limiting the search for surface damage or irregularities of wafer 10 to a narrow section of the perimeter of wafer 10.

Since surface damage or irregularities of a wafer cannot be assumed to be limited to such a narrow section of the perimeter of wafer 10, the wafer 10 is subjected to rotational motion 20 around the central axis 19 of the wafer, in this manner exposing all sections that are contained in the perimeter of wafer 10 to the there-through passing of waves 15 and therefore to detection and analysis of surface damage or irregularities in all sections that are contained in the perimeter of wafer 10.

Figure 2:
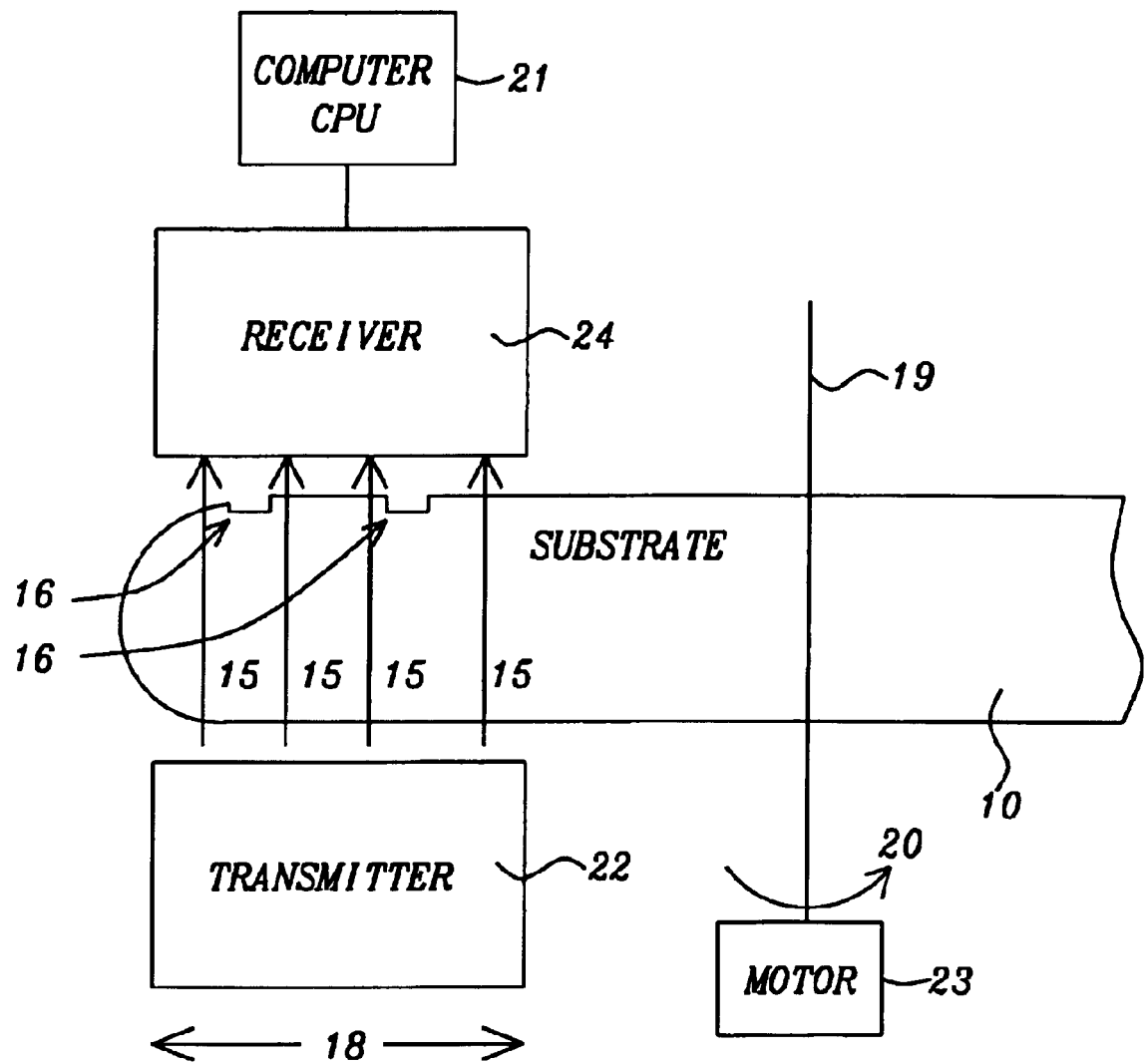
FIG. 2 is a cross section of a wafer with a source of energy, comprising either ultrasonic or electromagnetic energy, being aimed at the surface of a wafer, the waves of energy pass through the wafer from a first surface to a second surface and are captured and analyzed by a receiver of energy after the waves have passed through the wafer. A computer Central Processing Unit (CPU) is part of the equipment arrangement.
Figure 3:
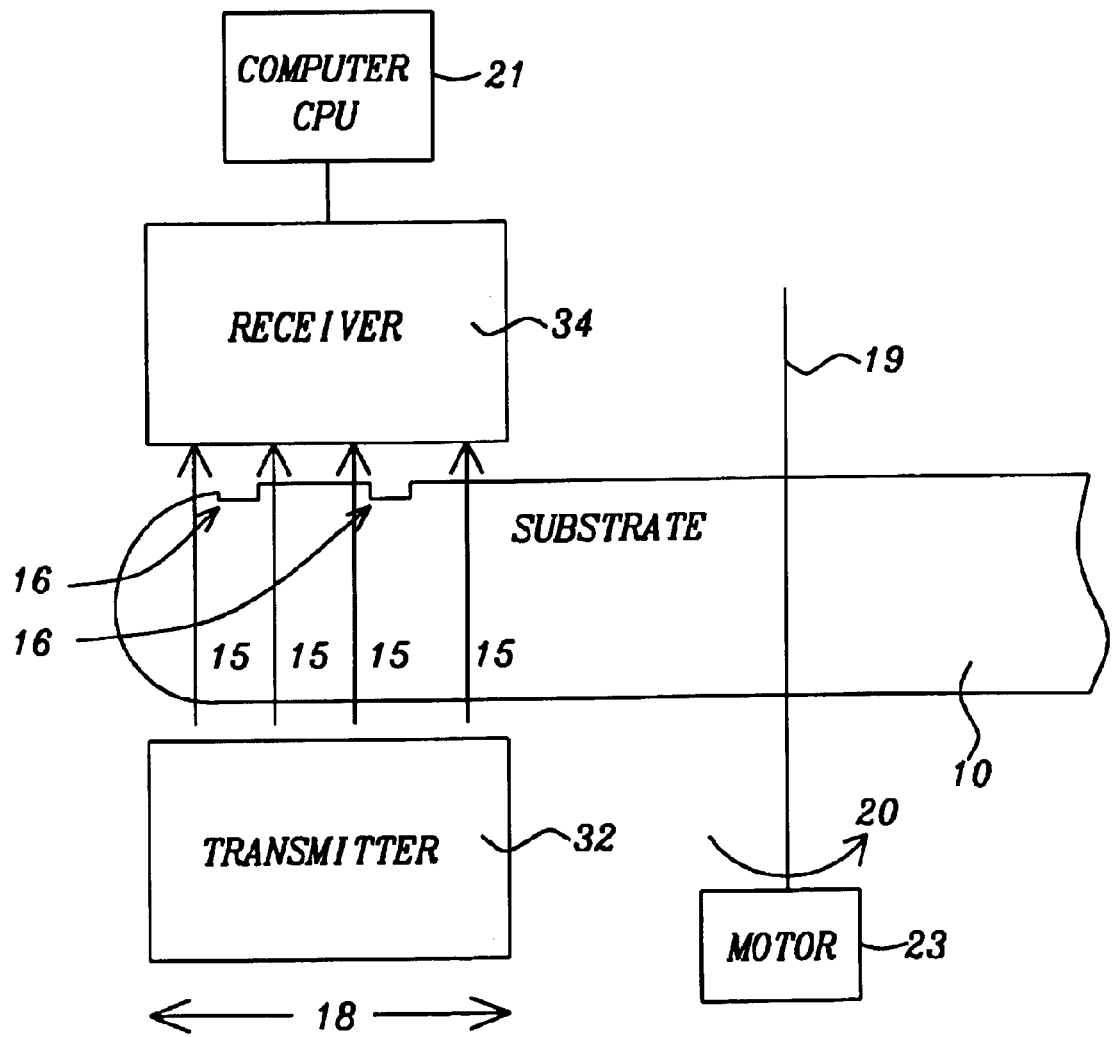
FIG. 3 is a cross section of a wafer with a movable source of energy, the source of energy being movable with respect to the first and second surface of a wafer. A computer Central Processing Unit (CPU) is part of the equipment arrangement.
Figure 4:
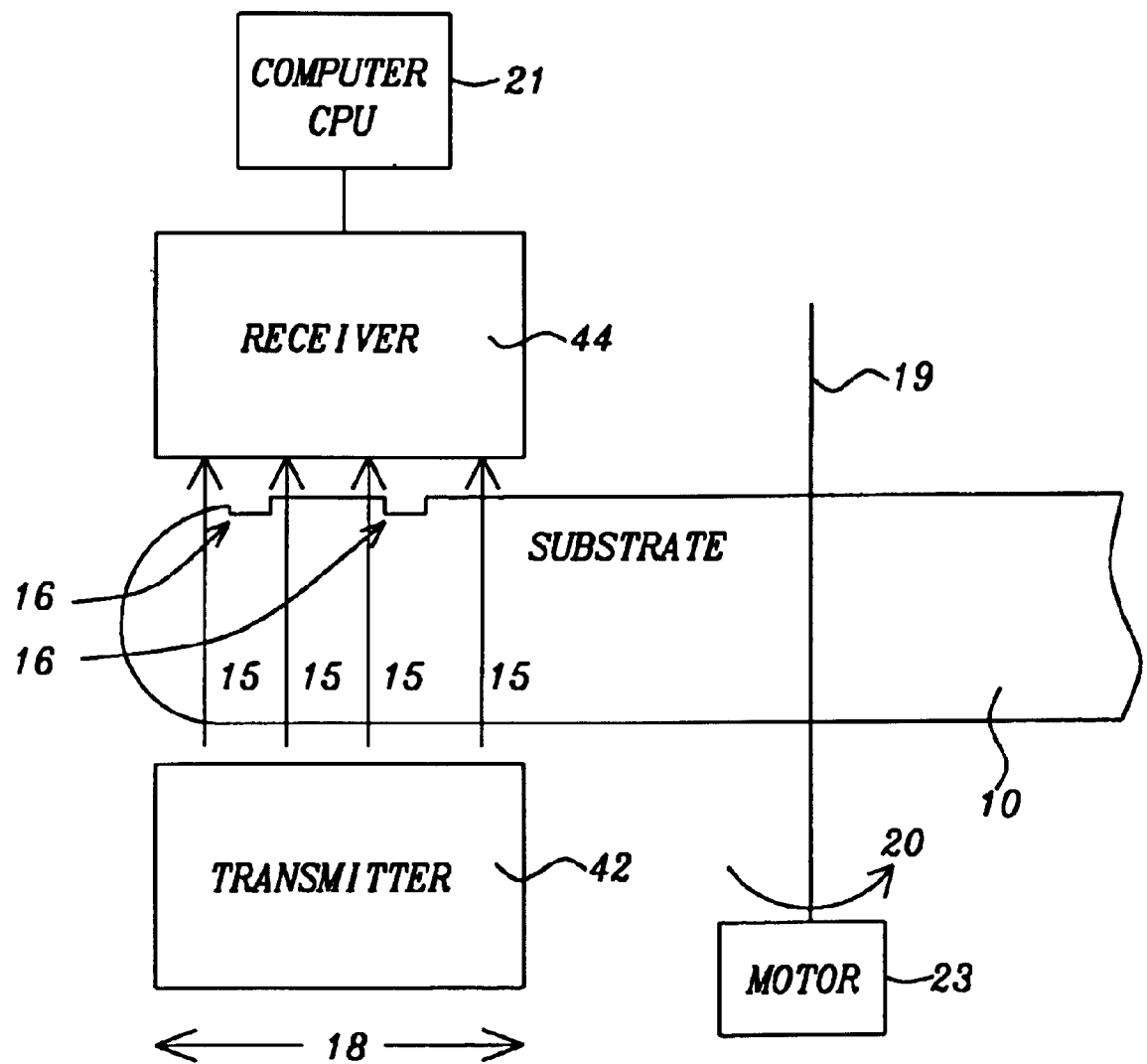
FIG. 4 is a cross section of a wafer with a hand-held source of energy. A computer Central Processing Unit (CPU) is part of the equipment arrangement.

FIGS. 2 through 4 further highlight additional applications of the invention, as follows:

FIG. 2 is a cross section of a wafer with a source 22 of energy, comprising either ultrasonic or electromagnetic energy, being aimed at the surface of a wafer, the waves of energy pass through the wafer from a first surface to a second surface and are captured and analyzed by a receiver 24 of energy after the waves have passed through the wafer.

FIG. 3 is a cross section of a wafer with a movable source 32 of energy, the source of energy being movable with respect to the first and second surface of a wafer, and a receiver 34 of energy.

FIG. 4 is a cross section of a wafer with a hand-held source 42 of energy and a receiver 44 of energy.

From the above description it is clear that:

1. By exposing the perimeter of a wafer to ultrasonic waves and by passing these ultrasonic waves through the wafer, conclusions can be drawn that relate to the condition of the wafer in the perimeter of the wafer, and more specifically to the presence or absence of damage in any form that may have been inflicted on the wafer 2. The highlighted method excludes human observation of the wafer itself and therefore excludes the introduction of human error 3. The highlighted method lends itself to automation, since all steps of error observation and analysis can readily be machine controlled and computer analyzed 4. The highlighted method lends itself to a high level of sophistication in detection wafer damage or surface irregularities since each type of wafer damage or surface irregularities can be recognized by its "footprint"

5. The highlighted method lends itself to significantly increasing the speed and therefore the throughput of the process of wafer inspection 6. The highlighted method is not limited to applications using ultrasonic technology but can be applied using any transmitting and receiving medium that transmits and receives energy that can be transmitted through a wafer 7. The highlighted method is not limited to analyzing wafers for the purpose of detecting wafer damage or surface irregularities but can be extended to any medium under investigation that allows the passing there-through of energy in the form of electromagnetic waves 8. The highlighted method is not limited to having an energy transmitter and receiver being placed in a stationary position with respect to the wafer that is being inspected for damage but can be extended to include hand-held emitting and receiving devices, which can be moved with respect to the wafer that is being inspected for damage.

The invention, which provides a method and apparatus of wafer damage inspection, can be summarized as follows:

providing a wafer providing a source of energy, comprising either ultrasonic or electromagnetic energy aiming waves of energy under an angle at the surface of the wafer allowing the waves of energy to pass through the wafer from a first surface to a second surface capturing waves having passed through the wafer analyzing the captured waves the source of energy comprising ultrasonic energy the angle being about ninety degrees the analyzing the captured waves is identifying deviations of the captured waves from known wave characteristics of reference the characteristics of the known wave characteristics of reference being selected from the group consisting of wave amplitude and wave frequency content and wave frequency spectrum and wave phase shift the source of energy being stationary with respect to a first and second surface of the wafer the source of energy being movable with respect to the first and second surface of the wafer the source of energy being a hand-held device aiming the waves of energy at the surface of the wafer being limited to aiming the waves of energy at a perimeter of the wafer the analyzing captured waves is identifying deviations of the captured waves from known wave characteristics of reference, the reference comprising the waves of energy aimed at the surface of the wafer under an angle the characteristics of the known wave characteristics of reference being selected from the group consisting of wave amplitude and wave frequency content and wave frequency spectrum and wave phase shift further extending the method by automating and bringing under computer control the steps of aiming the waves of energy at the surface of the wafer under an angle with the surface of the wafer, allowing the waves of energy to pass through the wafer from a first surface to a second surface, of capturing waver having passed through the wafer, and of analyzing the captured waves, and the analyzing the captured waves being extended to comprise classifying analysis results and correlating the analysis results with type of wafer damage, thereby creating a footprint of the wafer damage.

Although the invention has been described and illustrated with reference to specific illustrative embodiments thereof, it is not intended that the invention be limited to those illustrative embodiments. Those skilled in the art will recognize that variations and modifications can be made without departing from the spirit of the invention. It is therefore intended to include within the invention all such variations and modifications which fall within the scope of the appended claims and equivalents thereof.

What is claimed is:

1. A method of wafer damage inspection, comprising the steps of:

providing a wafer having a first surface and a therewith essentially parallel second surface, said wafer may or may not have been provided with active semiconductor devices over the surface thereof;

providing a hand-held source of energy, being movable with respect to the first and second surface of said wafer, therewith supplying waves of energy, said waves of energy having an energy content being sufficient for passing through said wafer from a first surface to second surface;

aiming said waves of energy at the surface of said wafer under an angle with the surface of said wafer, allowing said waves of energy to pass through said wafer from a first surface to a second surface;

capturing waves having passed through said wafer; and analyzing said captured waves.

2. The method of claim 1, said source of energy comprising ultrasonic energy.

3. The method of claim 1, said angle being about ninety degrees.

4. The method of claim 1, said analyzing said captured waves is identifying deviations of said captured waves from known wave characteristics of reference.

5. The method of claim 4, said characteristics of said known wave characteristics of reference being selected from the group consisting of wave amplitude and wave frequency content and wave frequency spectrum and wave phase shift.

6. The method of claim 1, said aiming said waves of energy at the surface of said wafer being limited to aiming said waves of energy at a perimeter of said wafer.

7. The method of claim 1, said analyzing said captured waves is identifying deviations of said captured waves from known wave characteristics of reference, said reference comprising said waves of energy aimed at the surface of said wafer under an angle.

8. The method of claim 7, said characteristics of said known wave characteristics of reference being selected from the group consisting of wave amplitude and wave frequency content and wave frequency spectrum and wave phase shift.

9. The method of claim 1, said method further being extended by automating and bringing under computer control said steps of:

aiming said waves of energy at the surface of said wafer under an angle with the surface of said wafer, allowing said waves of energy to pass through said wafer from a first surface to a second surface;

capturing waves having passed through said wafer; and analyzing said captured waves.

10. The method of claim 1, said analyzing said captured waves being extended to comprise: classifying analysis results; and correlating said analysis results with type of wafer damage, thereby creating a footprint of said wafer damage.

11. The method of claim 1, said source of energy comprising electromagnetic energy.

12. An apparatus for wafer damage inspection, comprising:

A hand-held source of energy, supplying waves of energy, said waves of energy having an energy content being sufficient for passing through a wafer from a first surface to a second surface, wherein the source of energy is movable with respect to the first and second surface of said wafer;

Said waves of energy being aimed at the surface of said wafer under an angle with the surface of said wafer, allowing said waves of energy to pass through said wafer from a first surface to a second surface of said surface;

means for capturing waves having passed through said wafer; and means for analyzing said captured waves.

13. The apparatus of claim 12, said source of energy comprising ultrasonic energy.

14. The apparatus of claim 12, said angle being about ninety degrees.

15. The apparatus of claim 12, said means for analyzing said captured waves comprising identifying deviations of said captured waves from known wave characteristics of reference.

16. The apparatus of claim 15, said characteristics of said known wave characteristics of reference being selected from the group consisting of wave amplitude and wave frequency content and wave frequency spectrum and wave phase shift.

17. The apparatus of claim 12, said waves of energy being aimed at the surface of said wafer being limited to aiming said waves of energy at a perimeter of said wafer.

18. The apparatus of claim 12, said means for analyzing said captured waves comprising identifying deviations of said captured waves from known wave characteristics of reference, said reference comprising said waves of energy aimed at the surface of said wafer under an angle.

19. The apparatus of claim 18, said characteristics of said known wave characteristics of reference being selected from the group consisting of wave amplitude and wave frequency content and wave frequency spectrum and wave phase shift.

20. The apparatus of claim 12, said apparatus further being extended by automating and bringing under computer control, thereby including:

Said waves of energy being aimed at the surface of said wafer under an angle with the surface of said wafer, allowing said waves of energy to pass through said wafer from a first surface to a second surface of said wafer;

Means for capturing waves having passed through said wafer; and

Means for analyzing said captured waves.

21. The apparatus of claim 12, said means for analyzing said captured waves being extended to comprise; analysis result having been classified; and said analysis results having been correlated with type of wafer damage, thereby creating a footprint of said wafer damage.

22. The apparatus of claim 12, said source of energy comprising electromagnetic energy.

* * * * *